United States Patent
Orgill et al.

(10) Patent No.: US 7,494,482 B2
(45) Date of Patent: Feb. 24, 2009

(54) METHODS AND APPARATUS FOR APPLICATION OF MICRO-MECHANICAL FORCES TO TISSUES

(75) Inventors: Dennis P. Orgill, Belmont, MA (US); Quentin Gavin Eichbaum, Watertown, MA (US); Sui Huang, Boston, MA (US); Chao-Wei Hwang, Brookline, MA (US); Donald E. Ingber, Boston, MA (US); Vishal Saxena, Cambridge, MA (US); Evan Stuart Garfein, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 907 days.

(21) Appl. No.: 10/146,472

(22) Filed: May 15, 2002

(65) Prior Publication Data

US 2003/0108587 A1    Jun. 12, 2003

Related U.S. Application Data

(60) Provisional application No. 60/291,120, filed on May 15, 2001.

(51) Int. Cl.
  *A61F 2/00* (2006.01)
  *A61F 13/00* (2006.01)
  *A61F 2/06* (2006.01)
(52) U.S. Cl. .............. 604/305; 604/304; 623/1.12; 623/1.22; 424/423; 424/426
(58) Field of Classification Search ......... 604/305–308, 604/304; 623/1–1.23, 1.44, 1.46–1.48; 606/191, 606/192; 424/423, 426
  See application file for complete search history.

(56) References Cited

U.S. PATENT DOCUMENTS 4,044,404 A * 8/1977 Martin et al. .............. 623/1.54
4,060,081 A   11/1977 Yannas et al. ............... 128/156

(Continued)

FOREIGN PATENT DOCUMENTS

WO    WO 2005/046762 A1    5/2005

OTHER PUBLICATIONS

Juutilainen, T et al, "Biodegradable wire fixation in oleacranon and patella fractures combined with biodegradable screws or plugs and compared with metallic fixation", Archives of Orthopaedic and Trauma Surgery, 114:6, Abstract only, 1995. http://www.springerlink.com/content.*

(Continued)

*Primary Examiner*—Tatyana Zalukaeva
*Assistant Examiner*—Melanie J Hand
(74) *Attorney, Agent, or Firm*—Wolf, Greenfield & Sacks, P.C.

(57) ABSTRACT

Methods and devices for transmitting micromechanical forces locally to induce surface convolutions into tissues on the millimeter to micron scale for promoting wound healing are presented. These convolutions induce a moderate stretching of individual cells, stimulating cellular proliferation and elaboration of natural growth factors without increasing the size of the wound. Micromechanical forces can be applied directly to tissue, through biomolecules or the extracellular matrix. This invention can be used with biosensors, biodegradable materials and drug delivery systems. This invention will also be useful in pre-conditioned tissue-engineering constructs in vitro. Application of this invention will shorten healing times for wounds and reduce the need for invasive surgery.

5 Claims, 10 Drawing Sheets

U.S. PATENT DOCUMENTS

| | | | |
|---|---|---|---|
| 4,215,679 A | 8/1980 | Rustin | 128/25 |
| 4,280,954 A | 7/1981 | Yannas et al. | 260/123.7 |
| 4,382,441 A | 5/1983 | Svedman | |
| 4,587,101 A * | 5/1986 | Marsoner et al. | 422/56 |
| 4,817,594 A * | 4/1989 | Juhasz | 602/42 |
| 4,921,483 A * | 5/1990 | Wijay et al. | 604/103.1 |
| 5,152,757 A | 10/1992 | Eriksson | 604/305 |
| 5,423,778 A | 6/1995 | Eriksson et al. | 604/305 |
| 5,636,643 A | 6/1997 | Argenta et al. | 128/897 |
| 5,645,081 A | 7/1997 | Argenta et al. | 128/897 |
| 5,661,132 A | 8/1997 | Eriksson et al. | 514/44 |
| 5,662,625 A | 9/1997 | Westwood | 604/305 |
| 5,701,917 A | 12/1997 | Khouri | 128/897 |
| 5,759,570 A * | 6/1998 | Arnold | 424/443 |
| 5,833,641 A | 11/1998 | Curtis et al. | |
| 5,876,432 A * | 3/1999 | Lau et al. | 623/1.13 |
| 5,904,659 A | 5/1999 | Duarte et al. | |
| 5,951,502 A | 9/1999 | Peeler et al. | 601/149 |
| 5,960,497 A | 10/1999 | Castellino et al. | 5/730 |
| 6,071,267 A | 6/2000 | Zamierowski | |
| 6,135,116 A | 10/2000 | Vogel et al. | 128/898 |
| 6,142,982 A | 11/2000 | Hunt et al. | 604/313 |
| 6,162,232 A | 12/2000 | Shadduck | 606/131 |
| 6,282,444 B1 * | 8/2001 | Kroll et al. | 607/3 |
| 6,296,617 B1 | 10/2001 | Peeler et al. | 601/152 |
| 6,420,622 B1 | 7/2002 | Johnston et al. | |
| 6,458,109 B1 * | 10/2002 | Henley et al. | 604/304 |
| 6,479,072 B1 | 11/2002 | Morgan et al. | |
| 6,514,515 B1 * | 2/2003 | Williams | 424/424 |
| 6,553,998 B2 | 4/2003 | Heaton et al. | |
| 6,613,082 B2 * | 9/2003 | Yang | 623/1.42 |
| 6,632,656 B1 | 10/2003 | Thomas et al. | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,735,468 B2 * | 5/2004 | Treppo et al. | 600/547 |
| 6,755,807 B2 | 6/2004 | Risk, Jr. et al. | |
| 6,767,194 B2 | 7/2004 | Jeon et al. | |
| 6,855,135 B2 | 2/2005 | Lockwood et al. | |
| 6,867,342 B2 | 3/2005 | Johnston et al. | |
| 6,899,873 B2 | 5/2005 | Ma et al. | |
| 6,939,569 B1 * | 9/2005 | Green et al. | 424/667 |
| 7,018,401 B1 * | 3/2006 | Hyodoh et al. | 623/1.12 |
| 2001/0007658 A1 | 7/2001 | Usala et al. | |
| 2002/0009805 A1 * | 1/2002 | Nevo et al. | 435/366 |
| 2002/0052570 A1 | 5/2002 | Naimer | 602/53 |
| 2002/0068913 A1 | 6/2002 | Fleischmann | |
| 2002/0095202 A1 * | 7/2002 | Schmidt | 607/122 |
| 2002/0115967 A1 | 8/2002 | Svedman | |
| 2002/0127736 A1 | 9/2002 | Chou et al. | |
| 2002/0150720 A1 | 10/2002 | Howard et al. | |
| 2002/0156470 A1 * | 10/2002 | Shadduck | 606/41 |
| 2003/0225347 A1 | 12/2003 | Argenta et al. | |
| 2004/0243073 A1 | 12/2004 | Lockwood et al. | |
| 2005/0004534 A1 | 1/2005 | Lockwood et al. | |
| 2005/0251083 A1 | 11/2005 | Carr-Brendel et al. | |

OTHER PUBLICATIONS

Dike, Laura E. et al., "Geometric Control of Switching Between Growth, Apoptosis, and Differentiation During Angiogenesis Using Micropatterned Substrates," Journal of the Society for In Vitro Biology, vol. 35, No. 8, Sep. 1999, pp. 441-448.

VAC Therapy. An Advanced System for Wound Healing [online]. Kinetic Concepts, Inc. [Retrieved on May 14, 2002]. Retrieved from the Internet: <URL: http://www.kcil.com/products/vac/index.asp>.

New Medicare Code Okays Home Treatment. [online]. Kinetic Concepts, Inc. [Retrieved on Jul. 29, 2004]. Retrieved from the Internet: <URL: http://www.web.archive.org/web/20010124074000/www.kcil.com/vacmedb.html>.(Web page of Kinetic Concepts, Inc. as archived by archive.org on Jan. 24, 2001.).

Kinetic Concepts, Inc., San Antonio, Texas-main page. [online]. Kinetic Concepts, Inc. [Retrieved on Jul. 29, 2004]. Retrieved from the Internet: <URL: http://www.web.archive.org/web/20001202010200/http://www.kcil.com/>.(Web page of Kinetic Concepts, Inc. as archived by archive.org on Dec. 2, 2000.).

Wound Care Devices: Vacuum Assisted Closure Therapy: The V.A.C. [online]. Kinetic Concepts, Inc. [Retrieved on Jul. 29, 2004]. Retrieved from the Internet: <URL: http://www.web.archive.org/web/20010302111623/www.kcil.com/the_v.a.c..html>.(Web page of Kinetic Concepts, Inc. as archived by archive.org on Mar. 2, 2001.).

Wound Care Devices: Vacuum Assisted Closure Therapy: The miniV. A.C. [online]. Kinetic Concepts, Inc. [Retrieved on Jul. 29, 2004]. Retrieved from the Internet: <URL: http://www.web.archive.org/web/20010112205000/www.kcil.com/mini-vac.html>.(Web page of Kinetic Concepts, Inc. as archived by archive.org on Jan. 12, 2001.).

International Search Report dated May 27, 2005 (citing US 5,904,659, 4,817,594, 5,759,570, 4,587,101).

Chung, S. et al., 2003, "Plastic microchip flow cytometer based on 2- and 3-dimensional hydrodynamic flow focusing," Microsystem Technologies, 9: 525-533.

Unger M. A. et al., 2000, "Monolithic Microfabricated Valves and Pumps by Multilayer Soft Lithography," Science, 288: 113-116.

Whitesides G. M. & Stroock A. D., 2001, "Flexible Methods for Microfluidics," Physics Today Online, 1-8.

* cited by examiner

US 7,494,482 B2

METHODS AND APPARATUS FOR APPLICATION OF MICRO-MECHANICAL FORCES TO TISSUES

CROSS-REFERENCE TO RELATED APPLICATION

This application claims the benefit of U.S. Provisional Application No. 60/291,120, filed May 15, 2001, the entire disclosure of which is hereby incorporated by reference.

GOVERNMENT SUPPORT

This invention was made with Government support under Grant/Contract No. 5R01-CA-055833-09 awarded by the National Institute of Health. The Government may retain certain rights in this invention.

FIELD OF THE INVENTION

The invention relates to the promotion of tissue growth and wound healing in general and more specifically to the application of micro-mechanical forces to promote tissue growth and wound healing in mammals and in artificial tissue or tissue explants in vitro.

BACKGROUND OF THE INVENTION

Over one million new chronic wounds develop in the United States each year with estimated treatment costs of $7 billion. Scores of new wound healing products are developed annually, yet wounds continue to be a significant public health problem as our population ages and as rates of diabetes mellitus increase. Wounds can be conceptualized as defects in protective skin coverage. Without this physiological barrier, wounds desiccate and are invaded by microorganisms leading to potential infection, with progressive tissue and fluid loss. The inability to heal lower extremity wounds often leads to amputation. There are several etiologies for chronic wounds, including trauma, burns, radiation, venous stasis, chronic infection, and systemic diseases such as diabetes. Current methods for improving wound healing emphasize effective drainage, prevention of infection, reduction of inflammation and minimization of tissue and fluid loss.

Most chronic wounds are characterized by a loss of cells and connective tissue matrix from at least the outer layer of skin (epidermis) and often also from the lower layer of skin (dermis) and deeper structures such as fat, muscle and bone. Closure of large wounds requires the production billions of cells, nutrition through a vascular network and mechanical strength from proteins and glycosaminoglycans present in a nascent extracellular matrix (ECM). To date, most research on wound healing acceleration has focused on soluble growth factors (i.e. FGF, PDGF, TGF-β, VEGF) that naturally stimulate cell proliferation, migration, ECM deposition and angiogenesis. However, the application of cytokines to wounds remains difficult because of the complex, concerted interaction between these factors and their very short half-life in vivo. Moreover, soluble chemicals alone fail to provide structural guidance to rebuild the tissue architecture.

Mechanical forces are well known to have a fundamental role in biologic systems. In development, forces of developing muscles affect bone formation. In addition the application of mechanical forces has been an important adjunct to surgery. Distraction osteogenesis allows gradual lengthening of bone. Tissue expansion allows gradual lengthening of soft tissues, including nerves and blood vessels. Tension wound-approximation devices close wounds over time. Application of sub-atmospheric pressure to wounds has been shown to increase the vascular supply within the wound and to accelerate healing. All of the above forces are directed at the wound in a single dimension and applied evenly over large areas (greater than 1 $cm^2$).

SUMMARY OF THE INVENTION

This invention relates to the development of devices that permit the application of micro-mechanical forces (MicMFs) to promote tissue growth and wound healing in mammals. The same technology may be used to promote the growth and development of artificial tissues or tissue explants in vitro. Given an aging population and the increasing prevalence of diabetes (a major cause of chronic wounds) this invention will find broad usage in health care for wound repair, tissue reconstruction, and potentially organ replacement. Accelerating wound healing reduces complications including infection, limb loss and pain. Secondary economic gains will result from reduced hospital stays, wound treatments, and medical care for chronically ill patients.

The paradigm for wound healing upon which the invention is based circumvents the daunting complexity of using the right mixture of growth factors at the right time by taking advantage of the observation that topological and mechanical force cues sensed by individual cells play a natural role in promoting cell proliferation according to local needs. Referring to FIG. 1, ample cell culture experiments have demonstrated that MicMFs exerted on individual cells can switch on specific genes that cause cell proliferation and regulate various cell functions critical for tissue development. Such a control mechanism has been implicated in wound healing. The invention consists of a set of devices and methods that exploit these physical and local cues, in addition to growth factors, to enhance wound healing.

This disclosure will focus on the development of methods to locally concentrate and focus these mechanical forces on the micron to millimeter scale. The use of MicMFs will not only more efficiently deform cells and alter cell behaviors, such as growth, that are necessary for optimal tissue growth and repair, but also do so without altering the macroscopic anatomy of the wound. Analysis of how forces are distributed within tissues using finite element analysis or advanced sensing technologies provides new data for precision engineering of devices that can be used in conjunction with conventional methods of macroscale force application (e.g., referring to FIG. 2 use of tension, compression, shear, electromagnetic forces, pressure, osmotic, surface tension, gravity, etc.) to concentrate MicMFs locally and thus, to exploit this new mitogenic pathway for improved wound healing. These devices are capable of concentrating stresses locally to induce precise cellular strains while applying forces over large tissue areas and may be adapted to apply forces on a continuous or cyclical basis. This methodology is especially useful for promoting wound healing, however, it also may be useful for stimulating growth or pre-conditioning of tissues in vitro, for example, to increase the wall strength of artificial blood vessels created using tissue engineering approaches.

This invention relates to devices and related methods for concentrating mechanical stresses locally on the millimeter to micron scale and methods to apply these stresses to cells within living tissues. This may be accomplished by engineering materials that induce local convolutions in the wound surface, topographic changes in the extracellular matrix that secondarily stretch cells, or direct deformation of cells that adhere to the device. These micro-mechanical strains stimulate wound healing by promoting cellular proliferation and migration, elaborating of natural soluble growth factors, and stimulating angiogenesis. The invention may comprise one or more of the following steps: coating micro-mechanical devices with extracellular matrix (ECM) factors, peptide fragments, synthetic molecules and growth factors to enhance cell proliferation, cell adhesion, and wound healing, combining MicMFs with exogenous growth factors and cytokines, optimization of MicMF application and drug delivery with mathematical modeling and feedback control, simultaneous localized and controlled delivery of drugs, proteins, and other factors to control edema, minimize infection and inflammation, and facilitate wound healing, employing the design of biodegradable, "smart-material" based devices that allow transmission of optimal MicMFs as they degrade, and fabrication of materials with micron to millimeter sized features, such as pores, which locally concentrate stress on adherent cells when forces are applied over large areas of the material.

The invention is based on the scientific insight that MicMFs play an important role in controlling cell proliferation. The presence of soluble growth factors alone does not optimize cell proliferation. For optimal proliferation, adherent cells, such as fibroblasts and endothelial cells, need to be stretched. Moreover, several forms of mechanical forces (i.e. stretch, turbulent flow shear stress, distortion, pressure, etc.) stimulate cell growth, migration, and other biochemical changes necessary for tissue growth and repair. Thus, forces applied to individual cells are critical in governing their response to soluble cytokines and ECM molecules. Physiologically, the non-muscle actin-myosin apparatus generates an isometric tension of the cytoskeleton. This process requires an ECM substrate (to which the cell is attached) that resists the "shortening" of the cell, thus allowing intracellular tension to build up to levels which are critical for cell growth.

In one embodiment, the invention relates to a device containing a material that contains multiple pores which when mechanically distorted concentrates stresses locally and focuses these micromechanical forces on adjacent living cells to promote their growth within living tissues. In one embodiment the pores are greater than 1 micrometer and less than 1 centimeter, and preferably greater than 20 micrometers and less than 2 millimeters. In another embodiment, the invention is constructed from non-degradable polymers including but not limited to polyurethane and polydimethylsiloxane. In another embodiment, the invention is constructed from biodegradable polymers including but not limited to collagen, fibrin, PLA, PGA, and PMA.

In other embodiments, pressure is applied through the application of vacuum or positive pressure. In another embodiment, the device is fabricated using microfabrication techniques, such as soft-lithography or conventional porous polymer fabrication strategies (e.g., salt leaching).

The invention also relates to a method of applying this above referenced materials to wounds or tissue grafts and exerting local mechanical distending forces at the micron to millimeter scale. These forces distend large regions (over 1 cm$^2$) of the material in order to accelerate tissue ingrowth and enhance tissue repair throughout the depth of the tissue without increasing the overall size or expanding the boundaries of the tissue (i.e., without causing wound opening or dehiscence). The invention also relates to a method of applying this device to promote growth and expansion of tissues in vitro by applying distending micromechanical forces throughout the depth of the tissue.

DETAILED DESCRIPTION OF PREFERRED EMBODIMENTS

Physical forces that are applied to tissues at the macroscale can trickle down to affect cell form and function. However, when these forces are applied homogeneously over large areas, the level of strain or deformation experienced by individual cells can be quite small, thus limiting the cellular response. In addition, global force applications typically result in a wide variety of stresses within a wound. Several devices are currently available that assist in wound healing by applying mechanical forces on the macroscale (evenly over areas greater than 1 cm$^2$) including tension wound closure devices, vacuum assisted closure and devices applied in distraction osteogenesis. This invention focuses on the development of methods and devices to locally concentrate forces applied on the macroscale within multiple smaller regions (less than 1 cm² and preferably less than 1 mm²), so as to amplify the forces that are experienced by individual cells on the microscale. One advantage of this method of MicMF application is the ability to induce cell stretch without increasing the size of the wound, thus minimizing the likelihood of wound dehiscence. One way to increase cell stretch is to create surface features within a device that induces three-dimensional convolutions within the wound. Accordingly, while exemplified in the following manner, the invention is not so limited and one skilled in the art will appreciate its wide range of application upon consideration thereof.

Figure 3A:
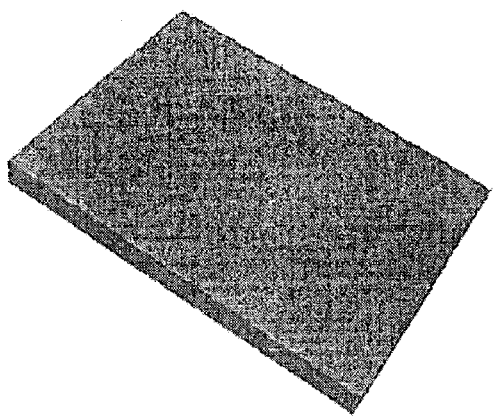
FIGS. 3A through 3D are schematic depictions of a wound as a flat surface with induced convolutions for uniaxial corrugation, multidimensional convolution, and rotational shear.
Figure 3B:
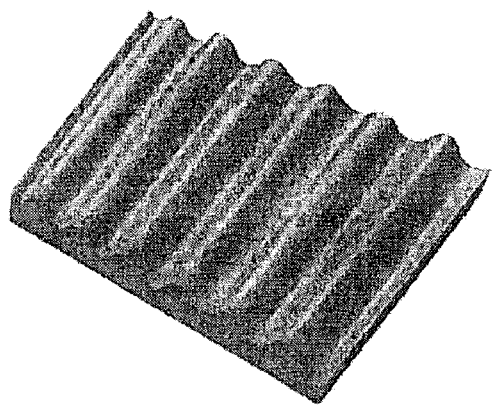
Figure 3C:
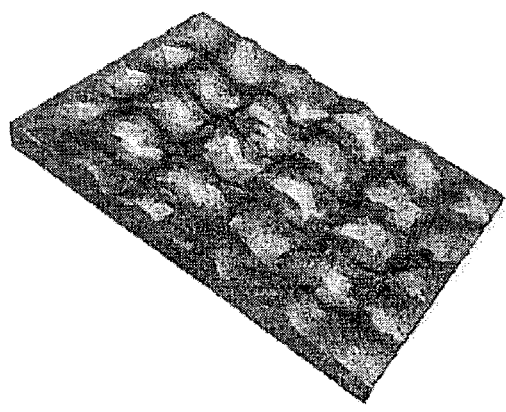
Figure 3D:
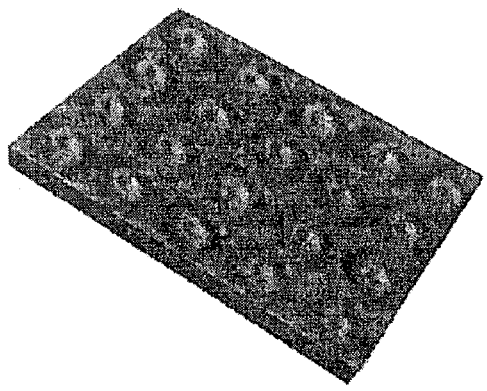

As depicted in FIGS. 3A through 3D, a wound can be conceptualized as a flat three-dimensional surface. Convolutions of the wound can be induced in a number of fashions including uniaxial corrugation, as depicted in FIG. 3B; multidimensional convolution, as depicted in FIG. 3C; and rotational shear, as depicted in FIG. 3D. After inducing localized convolutions in the wound by MicMFs, individual cells are stretched to a greater degree along the convoluted surfaces, thereby increasing the surface area of cells on the wound surface, without an increase in the overall wound size. The degree of convolution is directly related to the amount of cell stretch.

The general principle for force transmission into cells is explained as follows. The invention induces local cell strain using devices that apply MicMFs to multiple micro-regions of the wound without global wound extension. ECM receptors on the cell surface, such as integrins, sense and transduce the MicMFs to the cytoskeleton. Therefore, ideally, the therapeutically applied forces should be directed to the ECM and their interconnected receptors and cytoskeletal linkages. A general principle to increase force transfer efficiency is to coat the force generating device with biomolecules that bind directly to ECM components (e.g., heparin, antibodies to ECM components, such as collagen) or molecules such as fibronectin or RGD peptides that bind directly to cell surface integrin receptors. In vitro work to date on a variety of cell types suggest that different cell types exhibit different sensitivities to mechanical strain in terms of their growth response; different regions of tissues and wounds also may exhibit different sensitivities to force. Conventional medical devices that use forces therapeutically apply a single level of stress homogeneously over larger areas of tissue. Thus, it would be a great advantage to have devices that could apply optimal levels of deformation in appropriate micro-regions of a tissue and at appropriate frequencies or that vary in the level of stress that they apply within different areas of a single wound. The current invention provides both of these functions.

MicMFs originate from intrinsic stresses within structural molecules and body movements that transmit forces via distinct anatomic structures down to the cellular scale. Individual cells continuously perceive forces. MicMFs play an important role in governing cell proliferation and spatially orchestrating growth to meet tissue demand at the macroscopic. Thus, mechanical forces are key regulators of regeneration of functional tissue. Unlike the two-dimensional environment in which cell stretch pathways have been analyzed in vitro, cells in wounds exist in a complex three-dimensional network.

The physiology of fluids in the body can be divided into three compartments: 1) intravascular, 2) intracellular, and 3) extracellular. The intravascular component contains blood and its components and is responsible for the nutrition of other compartments through diffusion across capillary membranes. The extracellular compartment is comprised of structural extracellular matrix (ECM) proteins and glycosaminoglycans, salts and water. ECM proteins include several types of collagen, proteins (e.g., fibronectin, vitronectin and elastin). The ECM is in intimate contact with cells. Therefore, in vivo, MicMFs will often be transmitted through the ECM. In addition, the hydration state of the ECM will be a critical factor determining the magnitude and direction of forces transmitted to cells. For example, in edematous states, the ECM has excess water and swells. This can result in compression of the cells within the ECM making them less mitogenic. This can be seen in states such as lymphedma, venous stasis disease, burns and congestive heart failure. Application of forces that reduce edema will restore cells to their normal size and orientation resulting in cellular proliferation. The invention is directed at solving the challenge of minimizing wound dehiscence (separation) while maximizing mechanical stresses applied to individual cells on the micron scale within the depth of the wound. It provides methods and devices to improve and optimize wound healing by concentrating mechanical stresses exerted at the cell without having to increase macroscopic forces (such as overall stretch) applied to the whole issue that could compromise wound closure.

Figure 1:
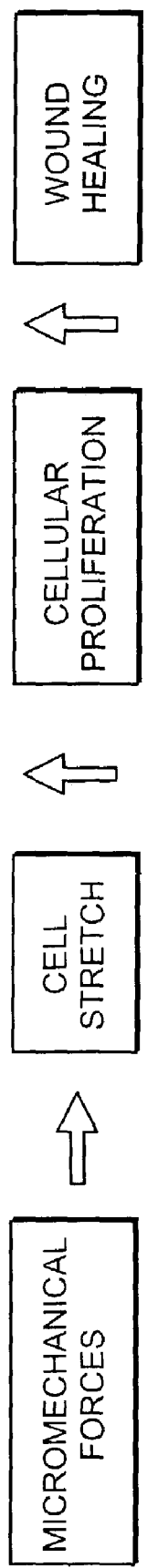
FIG. 1 is of block diagram indicating the generalized sequence of steps in an embodiment of the invention.
Figure 4:
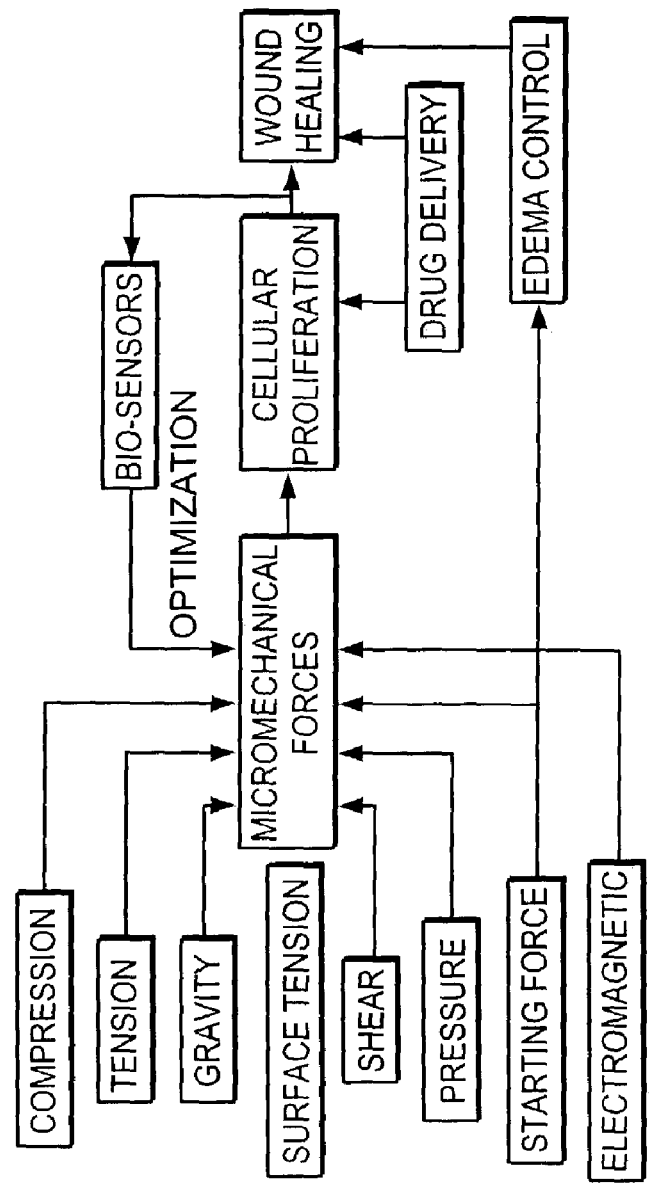
FIG. 4 is a block diagram indicating the sequence of integrated mechano-chemical wound healing acceleration according to an embodiment of the invention.
Figure 2:
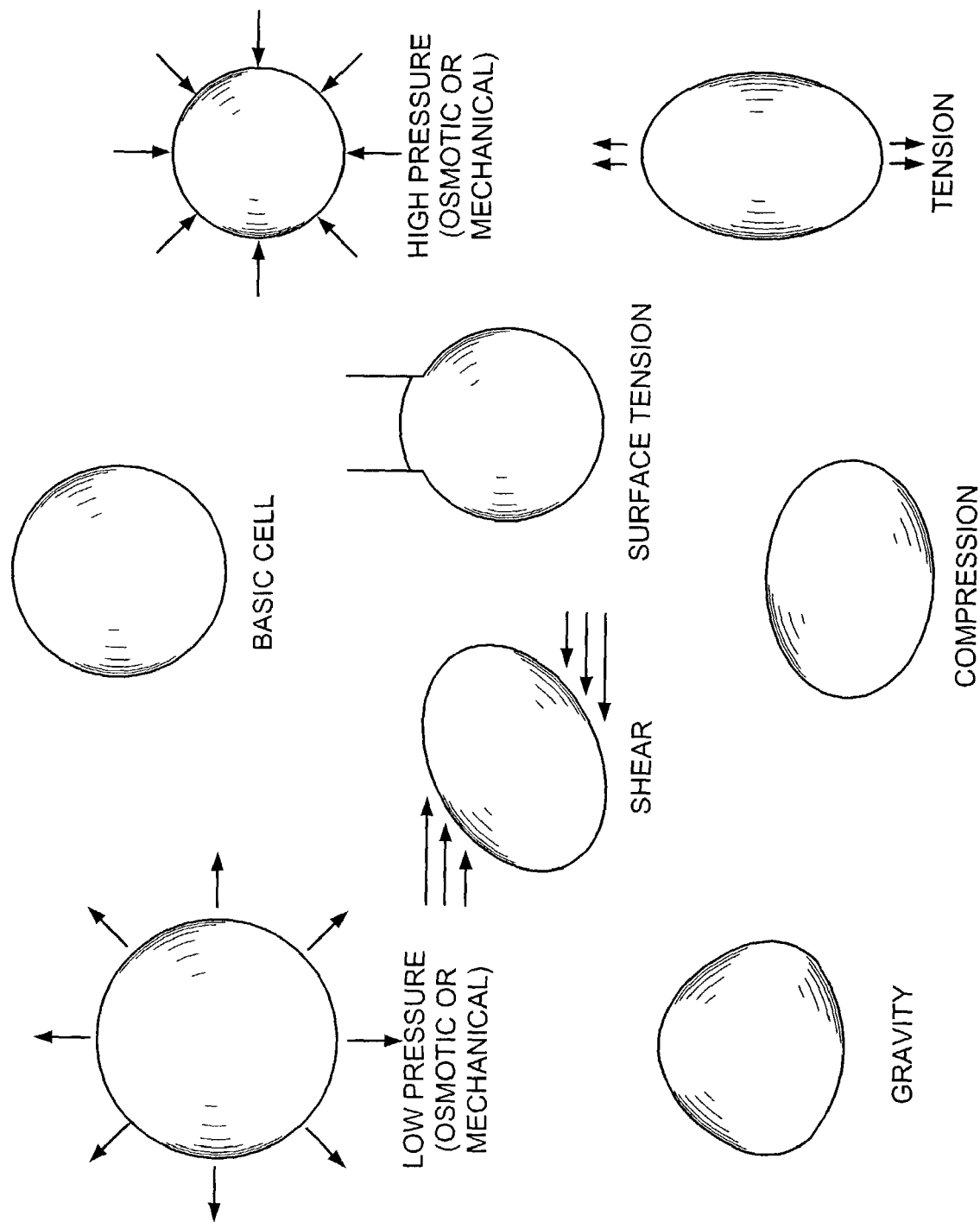
FIG. 2 is a schematic diagram of cell distortion induced by extrinsic forces including tension, compression, shear, surface tension, pressure, osmosis and gravity.

In generating and directing micromechanical forces to cells, the magnitude of forces must be controlled such that it is well in the physiological range. Most in vivo experiments suggest that maximum proliferative activity of cells that mediate wound healing—fibroblasts, endothelial cells, epithelium—occurs between 10 and 20 percent strain. This is important because wound healing is a dynamic process and local topology and cellular strains are expected to change in the course of healing. Therefore, the present invention involves development of devices or improvements in existing devices that concentrates stresses locally over multiple regions of a tissue surface in order to produce optimal cell deformation on the microscale. In an advanced design, the components that generate forces are integrated into a system with feedback control involving control elements such as Bio-Sensors or self-adapting ("smart") materials to further adjust the degree of cellular strain within the wound over time (see FIG. 4).

Mechanical stresses such as (1) compression and tension, (2) shear, (3) differential pressure that are applied evenly over a large surface area may be locally concentrated and focused using devices designed and fabricated with appropriate microarchitectural features, such as micron to millimeter-sized pores with controlled geometry, according to the present invention. The local forces would be selectively applied to cells in wounds to produce the appropriate strains and rates of strain necessary for optimal growth and repair. Both strain and edema can also be controlled through manipulation of (4) Starling forces. In addition, (5) Bio-Sensors and smart polymers could continuously monitor the degree of wound healing and provide feedback to the force generating device, resulting in a continually optimized level of applied load and strain. To further promote wound healing, drugs (antibiotics, mitogens) can be locally delivered, and (6) local biomolecular modifications can be made to enhance cell adhesion. Each of these components of the invention are independent modules that can be combined to create final products designed to meet practical needs, such as portability to allow for patient ambulation.

Figure 5:
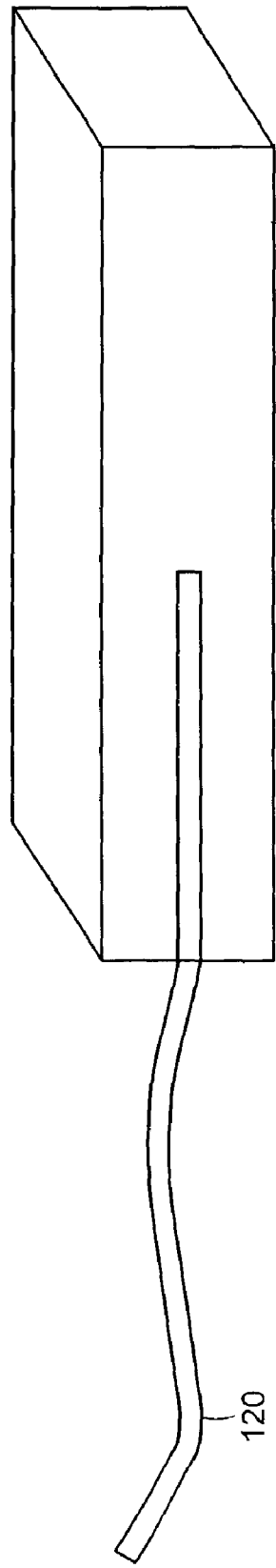
FIG. 5 is a schematic isometric diagram of a micromechanical force device according to an embodiment of the invention.

Referring to FIG. 5, one embodiment of the invention comprises a collagen sponge made primarily of Type I collagen using bovine Achilles heel or skin as a source. The pore size range of the sponge is 50 to 550 micrometers with a molecular weight between crosslinks of approximately 10,000 Daltons. The sponge is covered with a polyurethane occlusive dressing through which a tube exits that is connected to a vacuum of 50 to 200-mm Hg that is applied, continuously or cycled. The mechanical forces that are applied globally to the sponge surface are concentrated locally due to the geometric constraints of the pore shape, size and distribution. Over time, the intersticies within the mesh will be populated by vascularized outgrowths of tissue from the wound. The mesh acts as a temporary scaffold that is biodegraded over time as well as concentrate stresses locally. Every one to seven days, the sponge can be replaced and the process restarted. This device can be combined with a non-degradable sponge to transmit the sub-atmospheric pressure throughout larger wounds.

Figure 8A:
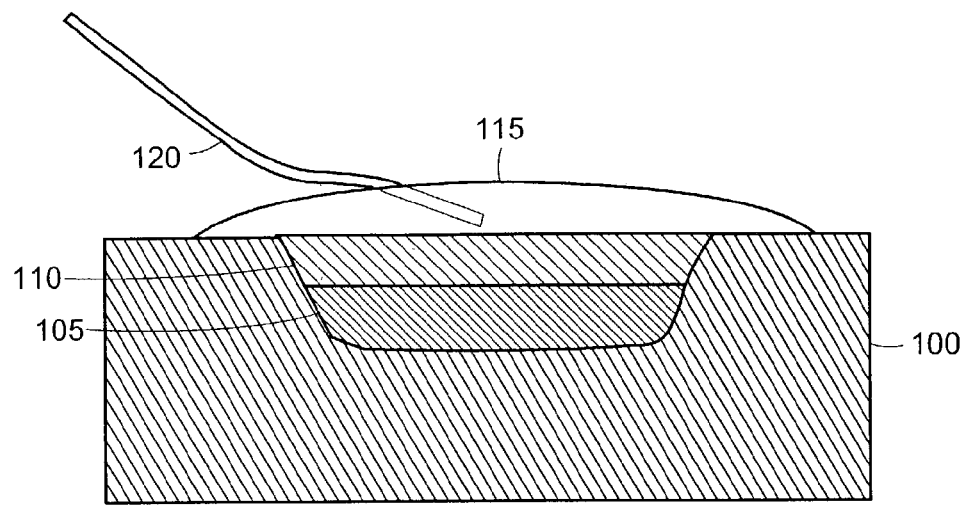
FIG. 8A is a schematic cross-section of a wound bed with an application of one embodiment of a therapeutic device according to the invention.
Figure 8B:
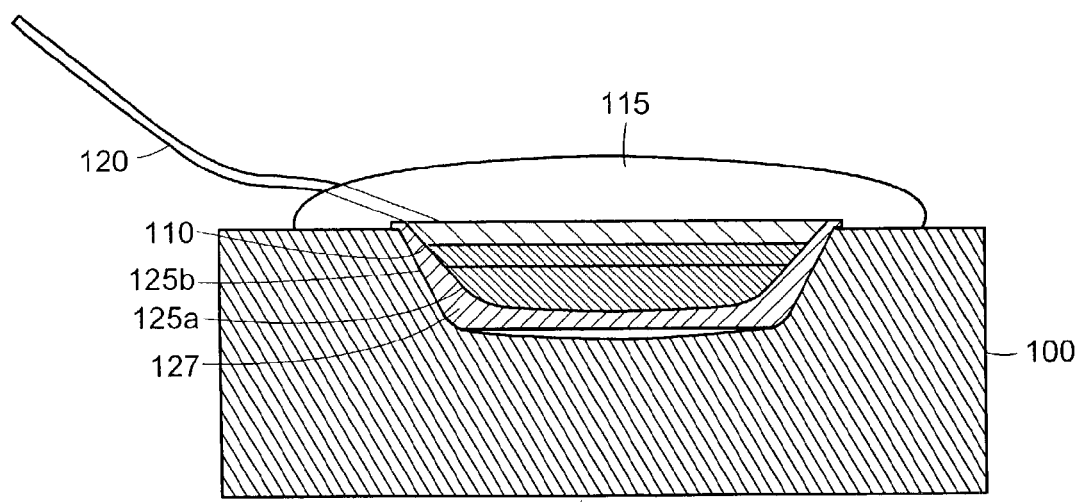
FIG. 8B is a schematic cross-section of a wound bed depicting tissue in-growth with the device of FIG. 8A.

A clinical application of one embodiment of the device is shown in FIG. 8A. A matrix of variable composition can be sized to the specific wound 100 is placed into the wound bed. The matrix includes a porous biodegradable matrix 105, a nondegradable sponge 110, and occlusive dressing 115, each applied in sequential layers to the wound 100. The pore size of the biodegradable matrix 105 is preferably between 50 and 1500 micrometers. Components of the different types of matrices, which are chosen depending on the characteristics of the wound may include natural polymers such as collagen, elastin, fibronectin, and laminin as well as synthetic polymers such as polyglycolic or polylactic acid. There will be a number of predetermined matrix compositions available for selection based on the specific wound 100. The biodegradable matrix 105 can be placed under vacuum or pressured via pressure tube 120. The matrices can be layered as depicted in FIG. 8B, one atop the other for deep wounds in a sequential manner as tissue ingrowth 127 occurs into the matrix with subsequent changes of the device. In this arrangement, the biodegradable matrix 105 further comprises a first matrix layer 125a and a second matrix layer 125b. The first matrix layer 125a would not be removed from the wound 100 during the healing process, but rather would become part of the wound 100, with native tissue in-growth over time.

Deep-layer strains can be introduced to wounds by the presence of a pressure gradient. Relative to the atmospheric pressure, the wound can be exposed either to a lower pressure (through the application of a vacuum) or to higher-pressure (through inflation of a sealed balloon) using currently available technologies, such as vacuum assisted closure and a tissue expansion device, respectively. Currently, pressure variations are usually applied globally with the whole wound subject to one pressure. The invention provides a method to concentrate these stresses locally, with specific areas of wounds subject to specific, and possibly different, pressures.

As an example of localized pressure application, an elastic sheet containing multiple small (less than 1 cm diameter and preferably less than 2 mm) pores can be affixed to the wound (e.g., using a surface coating of molecules that mediate ECM or cell adhesion) after which an applied vacuum stretches the exposed portions of the wound through the open pores of the sheet. In this system, the stiffness of the sheet needs to be greater than the stiffness of the wound, and the edges of the pores within the elastic sheet would be shaped appropriately to minimize trauma due to stretching. Alternatively, using high positive pressure, forces can be preferentially applied to the sheet and adherent cells relative to the neighboring non-adherent cells. With both methods, site-specific stretching can be accomplished with different pressures at different pores by varying pore size, shape and location. The shape and size of pores can be optimized using computer design and analysis to provide optimal concentrations of stresses locally. Flexible and rigid sheets containing pores with defined shape, size and location on the millimeter to submicron scales can be created using a variety of manufacturing methods, and microfabrication techniques including soft lithography. A "foam padding" adherent to the base elastic sheet can also be used for space filling and impact reduction. These materials can also be coated with polymers to enable controlled local delivery of drugs. The pressure can be set at an optimal value, or can be cycled at some optimum frequency corresponding to the optimal rate of strain to achieve cell proliferation.

Finite element analysis (FEA) can be used to evaluate the design of our pressure-based, porous elastic sheet, wound healing device. FEA is used to solve boundary value problems where closed form analytic solutions may be intractable. A mathematical model is used to model the geometry at discrete points, and the boundary of the modeled points is loaded with the forces and constraints that define the boundary conditions. Equations are set up by the solver based on the geometry that relate points inside the structure to points involving the boundary conditions.

In this exemplary analysis, a linear, homogeneous, isotropic model was constructed. By linearity it is meant that the stress strain behavior is linear over the strain ranges imposed. Homogeneous implies that the material has the same (average) properties from one part to another. Isotropic implies that the material responds uniformly in all directions. By using a linear assumption on the stress-strain response characteristic, the solver uses a small strain assumption. Thus the results are approximate, and may be validated with a large strain analysis using the correct stress-strain curve.

Referring to FIGS. 6A to 6D, the wound modulus of elasticity, sheet geometry, and applied pressure were treated as variable parameters. A one-dimensional model with a geometry defined by the typical pore width distance between the fibers (about 0.5 to 2 mm) was constructed. The skin was modeled with a constant thickness of 1 mm. The results of the modeling indicate that pore size of about 1.4 mm and a pressure of about 0.016 N/mm2 is sufficient to strain multiple local regions of the wound between 10 percent and 20 percent, the target range that has been shown to optimize cell proliferation.

In another embodiment, the device includes a porous FDA-approved, non-biodegradable material 110 (e.g., polyurethane, polydimethylsiloxane), either in a sponge configuration or as a sheet with pores designed and engineered (sized, shaped, and distributed) so as to optimally concentrate mechanical stresses locally and thereby promote tissue ingrowth in non-healing wounds or tissue grafts. The material is overlayed with the occlusive dressing 115, which may comprise a non-permeable solid sheet (e.g., silicone sheet) to ensure a good pressure seal. Mechanical distending forces are applied to this material through a portable, mechanical pump device linked by a pressure tube 120 that inserts into occlusive dressing 115. In another embodiment the device is driven by existing vacuum or positive pressure pumps or systems. This embodiment provides more rapid and complete wound healing; while allowing the patient to remain ambulatory.

In yet another embodiment the matrix material 105 may includes a porous FDA-approved, biodegradable such as collagen, PLA, PGA, PMA, or other suture material. The advantage of the biodegradable material is that the overlying silicon sheet "sloughs" off naturally as the polymer degraded thereby minimizing damage and tissue loss during each "dressing change". The integration of the polymer lattice with ingrown cells also accelerates mass-filling of the wound site. This material therefore shortens healing time, decrease morbidity, and provide a better cosmetic result.

Compression and tension may be useful for wound healing for various types of tissues. For instance, compression promotes bone healing and cartilage regeneration, whereas tension might be more helpful in soft tissue healing and osteogenesis. Neither compression nor tension results in a "purely" compressed or stretched state for the cell however. The tensegrity model of cellular architecture implies that because of the networked organization of the cytoskeleton, tension in one direction may induce compression in subcomponents within the cell, such as microtubules. Compression in one direction may induce extension and tension other structural components (e.g., microfilaments) within the cell. Stretching of cell surface adhesion receptors and cytoskeletal components alters cellular biochemistry and regulates genes for replication.

Cells within the wound can be subjected to a controlled strain using devices that can mechanically induce tension or compression in a steady or time-dependent manner as necessary. These devices can also be fabricated to enable to local delivery of drugs.

Stresses may also be generated by external mechanical devices. In one embodiment, biodegradable sheets or meshes, coated with natural ECM molecules, are draped on the wound and stretched or compressed. The coating of bioadhesive molecules interacts with ligands on the cells within the wound directly, so that stretch or compression of the coated sheet with an external device is transduced selectively and directly to the cells without re-opening the wound.

In one embodiment, a stiff biodegradable wire can be coiled around a compliant biodegradable tube (with a diameter of about 500 µm) coated with ECM proteins. Cells will be allowed to adhere to the surface. Upon subsequent inflation of the tube with fluid or air, the tube will protrude through the stiff coil, creating a local stretch of the adherent cells which is controlled by the degree of inflation. In a variation, a ECM protein-coated compliant tube can be positioned inside a stiff porous outer tube, such that on inflation, the inner tube protrudes through the pores of the outer tube, creating a local stretch. If the compliant tube is fabricated with dialysis-membrane size pores, the inflation fluid can also be used to deliver drugs or, by adjusting protein content, to carry away edema fluid.

In one embodiment, stress application to cells may be accomplished using magnetic forces. Paramagnetic or ferromagnetic beads coated with integrin-ligands (e.g., RGD, integrin) may be applied directly to cells on the surface of a wound. Upon application of an external magnetic force, the cell surface-bound beads experience a pulling or twisting force which is transduced to the cytoskeleton and enhances signal transduction. For example, using, ferromagnetic beads, a torque force can be applied: first, a magnetizing pulse is applied, followed by a twisting field in a different direction for 5-15 min. The process can be repeated cyclically.

In another embodiment, elastomeric membranes may be constructed containing magnetic microbeads (e.g., less than 10 microns in diameter) distributed throughout the material of the membrane and the surface of the membrane is coated with molecules that mediate adhesion to ECM and cells. This wound dressing is applied directly to the surface of the wound and mechanical stresses are applied locally to adherent cells on the micron scale by applying constant or varying homogeneous magnetic fields of various intensity across the surface of the entire wound. Altering the size, distribution, and magnetic moment of the beads can vary the local stresses applied. This method can be combined with porous sheets to further concentrate stresses and strains within preferred micro-regions.

In one embodiment, stress may be generated by intrinsic cellular contraction. A compression resisting or self-expanding non-malleable material that can hold its shape in tension without the aid of an external device will allow cells "to pull against" and thereby generate isometric tension. One example is a metallic or polymeric mesh/matrix coated with bio-adhesive molecules and affixed to the wound in a compressed or stretched form, which then returns to its original shape upon release or other stimuli. The entire assembly can be biodegradable. The coated bio-adhesive molecules interact with ligands on cells within the wound such that stretching and compression is transduced to the cells directly. Feedback and regulability of forces can be described as follows.

Self-expanding material can be fabricated from shape-memory alloys, such as nitinol, which can change shape with thermal variations. Applied stress can be made time-dependent to correspond to the optimal rate of strain for wound healing. This can be accomplished by fabricating the material from a system of interconnected nitinol tubes, through which fluid of varying temperature can be circulated or by applying electrical current.

Polyethers such as poly(ethylene glycol) (PEG), poly(propylene glycol) (PPG), and poly(tetramethylene glycol) (PTMG) can be copolymerized with oligomers of D,L-lactic acid and terminated with acrylate groups to form photopolymerizable biodegradable macromers. Photopolymerizable hydrogels may also be similarly fabricated. Either the hydrogel or polymer form of the material can be injected as a fluid (mixed with ECM proteins for cell adhesion) into the wound and polymerized to various desired stiffnesses by varying exposure to light. Since the material is initially fluid, it will inherently conform to the shape of the wound and seal it. Air bubbles can be incorporated into the fluid for desired porosity. Stiffness can be maintained as the material biodegrades by renewed light exposure or injection of more material. Biodegradation will be most rapid on wound periphery and slower in the core, matching where the cells most need space or anchor. Hydrogels can be made to swell if desired, providing an active cell stretching element. Drug delivery can also be easily incorporated into either the hydrogel or the polymer.

Smart material composed of different intercalating meshes of material offer corresponding disparate resistances to biodegradation. This allows the material to maintain stiffness even as it is continuously degraded proportionally to the increase in wound cellularity. Such a device would prevent early dissipation of the resisting force in the device and guarantee long-lasting effect. Examples of such smart materials are described below.

The time-dependent viscoelastic properties of the polymeric or metallic mesh can be optimized to match its rate of strain under stress to the optimal rate of strain for cellular proliferation. For polymers and hydrogels, viscoeleastic properties can be modulated by varying the degree of cross-linking within the polymer, and/or by varying the interfibrillar material. The strain response can be made anisotropic as desired by combining multiple polymers within the material.

Pre-programming the response through a ratchet-like arrangement affixed to the wound can finely control viscoelasticity. The spacing between the ratchet teeth can be set to provide the desired time-dependent viscoelastic response that matches the optimal stimulus required for cellular proliferation. The ratchet mechanism can be powered internally using a stretched spring, or externally, by using a pneumatic device. The ratchet advancement can be controlled by sequentially biodegradable teeth (teeth made of materials that biodegrade at various kinetics), or by using a pneumatic device. Multiple ratchets can be stacked to achieve anisotropic responses.

Shear forces produce a strain on the surface cells of the wound distinct from absolute stretch, and can also be conducive to cell proliferation. Methods used to generate shear stress are inherently coupled to the ability to control pressure that imparts deep-layer strains in addition to surface-level shear. Shear is created in all cases by moving fluids, which can be used as a vehicle to deliver drugs, carry away wastes, and control edema, by varying protein content in the fluid. Depending on the shearing mechanism, the shear can be applied in a time-dependent fashion by varying, imposed flows, imposed pressures, or imposed surface translations. The magnitude of the shear is dependent, in all embodiments, on the viscocity and velocity of the circulating fluid and on the distance between the wound and the device.

It is still unclear whether it is laminar shear or turbulent that is most useful in wound healing. Closed-form analysis is provided for laminar shear and simplified geometries for which such analysis is straightforward. In general, turbulence can be achieved using each of the devices by enlarging the geometry or increasing the flow such that the Reynolds number exceeds 2,00. Analysis of turbulent flow is inherently empirical, and thus will not be provided here; however, it should be noted that the laminar stress on the wound can be used to compute an approximation of the magnitude of the turbulent stress.

Global shear stress may be applied to the surface cells of the wound using fluid circulation. The wound is covered with a conduit through which an external device applies fluid flow. An opening is made in the conduit at the site of the wound and sealed onto surrounding intact tissue, exposing the wound to the fluid. The velocity profile and the fluid viscosity control the shear stress. The external device and the shape of the conduit determine the velocity and pressure. Fluid viscosity can be varied as desired by modulating its PEG content. The fluid may also be used to deliver drugs, carry away wastes, and control edema. To induce turbulence, the geometry and fluid velocity must be such that the Reynolds Number is greater than 2500. This method may be particularly useful for modulating the growth and viability of engineered tissues in vitro.

For steady, laminar flow Q provided by an external pump, and plane plastic sheet covering the wound at a distance H, the velocity profile is $$u(y) = \frac{3Q}{4H}\left(1 - \left(\frac{y}{H}\right)^2\right).$$

Given fluid viscosity $\nu$, the shear stress on the wound is $$\tau_{yx}(y = H) = -\frac{3\mu Q}{2H^2}.$$

The fluid viscosity can be time-dependent. Given a reference pressure $p_0$, the pressure distribution is $$p(x) = p_0 - \frac{3\mu Q}{2H^3}x.$$

For an imposed pulsatile pressure gradient $G=G_0(1+\epsilon \sin \omega t)$ with fluid kinematic viscosity $\nu$, and a cylindrical tube of radius R such that the Womersley number $$R = \frac{R^2/\nu}{\omega^{-1}} \ll 1,$$

the velocity profile beyond start-up time is $$\frac{u}{G_0 R^2/\nu} = \frac{1}{4}\left(1 - \left(\frac{r}{R}\right)^2\right)(1 + \sin\omega t) + R\frac{\cos\omega t}{64}\left(4\left(\frac{r}{R}\right)^2 - \left(\frac{r}{R}\right)^4 - 3\right) + O(R^2)$$

This corresponds to a relatively viscous fluid, with pressure oscillating at a relatively low frequency, in a small cylindrical tube. The shear stress on the wound is $$\tau_{rz} = \rho GR\left(\frac{R\cos\omega t}{16} - \frac{1 + \sin\omega t}{2}\right)$$

given fluid density $\rho$. The pressure distribution is $p(z)=p_0-G_0 z(1+\epsilon \sin \omega t)$ and is referenced to pressure $p_0$.

Shear stress can also be created by forcing fluid through thin slots or pinholes within a plate placed close to the wound. This system allows the site-specific control of shear stress within the wound, as areas of the wound adjacent to the thin slots will experience significantly higher shear stress than areas further away. High shear stress may created with very low fluid flow. Site-specific control may be useful in instances of uneven healing, when unhealed areas of the wound may need more stimulus than the healed areas. As with the external circulation system, the fluid viscosity can be varied as desired by increasing or decreasing its PEG content, and can be also used to deliver drugs, carry away wastes, and control edema by its osmolarity. To induce turbulence, the geometry and fluid velocity must be such that the Reynolds number is greater than 2,500.

An analysis of the single pinhole system, providing point-specific shear stress with laminar flow will be presented here as an illustration. For fluid injected with flow 2Q into a hole radius R0 at center of a disk of radius R located a distance 2H above the wound, the velocity profile is $$u_r = \frac{3Q}{4\pi rH}\left(1 - \left(\frac{z}{H}\right)^2\right)$$

assuming that the gap is thin (H/R<<1) and the injection hole is small (R0/R<<1). Given fluid viscosity m, the resulting shear stress is $$\tau_{rz} = -\frac{3\mu Q}{2\pi rH^2}$$

with r the distance from the pinhole. The 1/r dependence demonstrates the possibility of creating high shear stress locally with low flows. The resulting pressure distribution is also dependent on distance from the pinhole, and is $$p = p_0 - \frac{3\mu Q}{2\pi H^3} \ln r$$

when referenced to pressure $p_0$.

Figure 9:
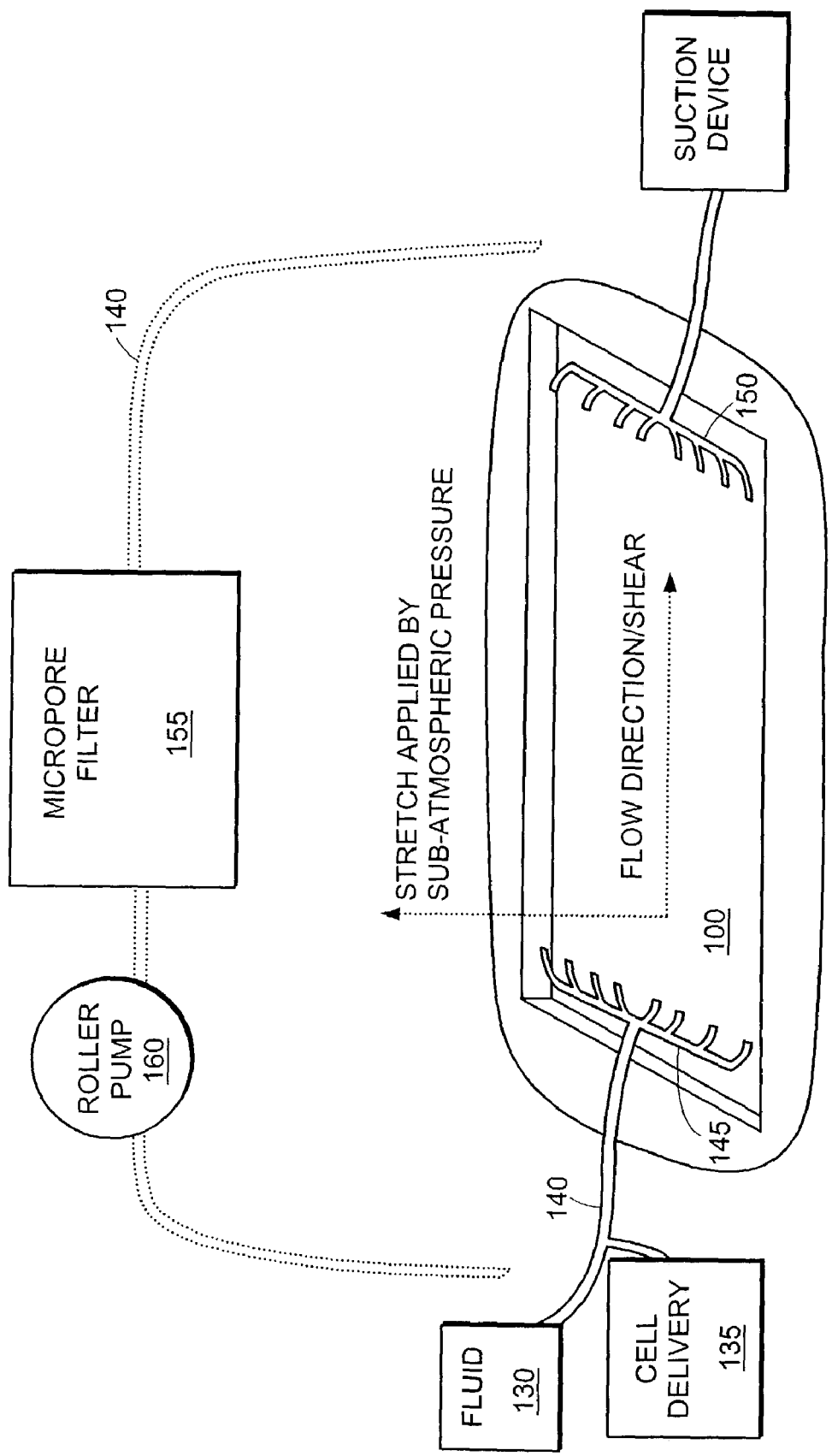
FIG. 9 is a schematic isometric diagram of a wound bed with an application of one embodiment of a therapeutic device, depicting a filtration, recirculation and nutrient delivery system.

FIG. 9 depicts a clinical application of another embodiment according to the invention. This embodiment adds an in-flow system for the delivery of fluids, and an outflow system for the removal of fluids and the application of a vacuum to the wound for integration with a biodegradable matrix 105 the overlying non-degradable sponge 110 such as polyurethane, and the occlusive dressing 115. The biodegradable matrix has been described. A polyurethane or polyvinyl alcohol sponge designed to provide both an air-tight seal for the system and to protect the wound 100 from infection. This embodiment allows unidirectional transport of fluids 130 and cell delivery 135 parallel to the surface of the wound 100. One end of the wound 100 has a distributed network of tubing that allows uniform application of fluid on one end of the wound through an inlet manifold 145. The other end of the wound has a distributed tubing network allowing for the egress of fluid through an egress manifold 150 via vacuum, pressure or siphon drainage. This fluid parallel to the surface applies a shear force to the wound 100 stimulating the wound cells to proliferate, and allowing transport of growth factors, oxygen, nutrients, antimicrobials and cells to the wound site. Egress of fluid allows for transport of waste products including carbon dioxide, bacteria, cytokines and nitrogenous breakdown products. In other embodiments. In a further embodiment, fluid collected in the egress manifold 150 is directed through a micropore 150 filter via the network tubing 140 and returned to the inlet manifold 145 by a prime moving source such as roller pump 160.

In another embodiment, a roller system may be employed to effect parallel translation. The translation of a surface parallel to the wound imparts motion to fluid in the gap between the translating surface and the wound, resulting in shear stress. For certain gap dimensions, tremendous positive pressure can be generated within the gap. This pressure, which can also be used to stretch cells and control edema, can be set as desired by varying the shape of the gap and the viscosity of the fluid. For fast enough translation, the motion of air in the gap may be enough to create adequate shear stress. To induce turbulence, the geometry and fluid velocity must be such that the Reynolds number is greater than 2500.

As an example, continuous parallel translation can be accomplished with a roller device, essentially a miniaturized version of the supermarket conveyor belt. Rollers with surfaces that can adapt to the contour of the wound can also be made through the use of a compliant material (thick rubber) which can be padded with sponge foam or built with multiple encased springs.

Under laminar flow conditions, for a thin fluid-filled gap h(x) between the wound and the roller surface of length L (h/L<<1), and translation velocity U(t), the velocity profile is $$u(y) = U\left(1 - \frac{y}{h(x)}\right) + \frac{1}{6h^3(x)}\left(\frac{Uh(x)}{2} - \frac{6\mu U}{L}\int_0^L \frac{dx}{h^2(x)}\right)(y^2 - yh(x))$$

The integral can be evaluated numerically depending on the particular shape of the roller h(x). The resulting shear stress on the wound, given a fluid viscosity of $\mu$ is $$\tau_{yx} = \frac{\mu U}{h(x)}\left[\frac{11}{12} - \frac{\mu}{Lh(x)}\int_0^L \frac{dx}{h^2(x)}\right]$$

The pressure distribution, referenced to a pressure $p_0$ is $$p(x) = p_0 - \int_0^x \frac{12\mu}{h^3(x)}\left(\frac{Uh(x)}{2} - \frac{6\mu U}{L}\int_0^L \frac{dx}{h^2(x)}\right)dx$$

The gap shape h(x), translation velocity U(t), and fluid viscosity $\mu$ can be adjusted as necessary to achieve both the desired shear stress and pressure distribution profile.

In one embodiment, perpendicular and multicomponent translation of a surface in a direction perpendicular to the wound imparts motion to fluid in the gap between the translating surface and the wound, resulting in radial motion and shear stress. For certain gap dimensions, large pressures can be generated within the gap. To induce turbulence, the geometry and fluid velocity must be such that the Reynolds number is greater than 2,500.

As an example, the oscillating perpendicular motion of a disk or a piston in an enclosed volume can force fluid within that volume to translate radially, with uniform time-dependent pressure throughout the wound. y combination of perpendicular, parallel, or rotational translation can also be used to create the appropriate shear stress, as desired.

For a flat plate at a distance h(t) from the wound moving with vertical velocity U(t), under laminar flow conditions, the radial velocity is $$u_r = \frac{3}{8}U\left(\frac{r}{h}\right)\left(1 - \left(\frac{z}{h}\right)^2\right),$$

and the vertical velocity is $$u_z = -\frac{3}{2}U\left(\frac{z}{h} - \frac{1}{3}\left(\frac{z}{h}\right)^3\right).$$

Given a fluid viscosity $\mu$, the shear stress is $$\tau_{zr} = \frac{3\mu Ur}{4h^2},$$

increasing away from the center of the plate. Given reference pressure $p_0$, the pressure distribution is $$p = p_0 - \frac{3}{8}\frac{\mu UR^2}{h^3}\left(1 - \left(\frac{r}{R}\right)^2\right).$$

The velocity distribution, shear stress, and pressure can all be time-dependent.

The generation of shear in a two-dimensional plane as previously described can be extended to a three-dimensional volume for severe wounds that form cavities. In this instance, a moving surface is inserted into the cavity, surrounded with fluid, and continuous motion is provided to generate the appropriate shear stress. Fluid viscosity and protein content can be adjusted to regulate shear stress and edema, and drugs can be delivered through the fluid. To induce turbulence, the geometry and fluid velocity must be such that the Reynolds Number is greater than 2,500.

As an illustration, a caged ball, inserted into the wound cavity, can be continuously rotated to generate the necessary stress in a cavity. The entire system can be made of biodegradable polymers, so that an additional operation will not be needed to retrieve the device after the wound has healed.

Starling forces dictate the fluid pressure balance in the wound milieu. The fluid transfer rate (J) across a membrane is given by $J=RS[(P_C-P_{IF})-(\pi_C-\pi_{IF})]$ where R is the hydraulic conductance of the membrane, S is the surface area, P is hydrostatic pressure and $\pi$ is the oncotic pressure in the cell (subscript C) and in the interstitial space (subscript IF). This relationship can be used to control wound edema, and also to induce cell strain.

Loss of endothelial integrity causes large proteins such as albumin to leak into the wound space, raising the interstitial oncotic pressure. Fluid consequently flows into the interstitial space, resulting in wound swelling (edema). Such edema can be minimized using our devices through the control of either hydrostatic pressure or oncotic pressure. The hydrostatic pressure can be controlled directly either by altering the pressure profile in the fluid flow devices (such as by changing flow conduit geometry or flow velocity), or through the mechanical application of pressure (such as with a vacuum or high pressure cell). Oncotic pressure might be controlled mechanically (such as by changing flow to alter protein washout and content), or through the actual delivery of oncotic proteins (such as albumin) within the flow.

Cells will swell or shrink depending on the net pressure drop across its membrane. The net effective pressure drop is essentially the difference between the hydrostatic pressure drop and the oncotic pressure drop across the cell membrane. By controlling these pressures, potentially in a time-dependent manner, it is thus possible to induce the cells to swell or shrink, thereby causing the appropriate cell strain. Pressures can be manipulated, as in the control of edema, by influencing both hydrostatic and oncotic pressures. The hydrostatic pressure can be controlled by altering the pressure profile in the fluid flow devices (such as by changing flow conduit geometry or flow velocity), or through mechanical application of pressure (such as with a vacuum or high pressure cell). Oncotic pressure might be controlled mechanically (such as by changing flow to alter protein washout and content), or through the actual delivery of oncotic proteins (such as albumin) within the flow.

Differences in surface energy between biomaterials and the wound can cause direct stresses and deformation on wounds. This is most easily appreciated in the common experiment demonstrating capillary action. Small porosity channels can induce specific forces on the wound resulting in cellular deformation. A device that used multiple small tubes oriented perpendicular to the wound would induce MicMFs on the wound. In alternative embodiments, a membrane with an array of different adjacent surface energies could result in micromechanical deformations of the wound.

Surface tension interactions at the wound surface can induce convolutions in the wound surface without the use of suction or vacuum. In this invention, porous materials are made of a small pore size 10 to 500 µm pores that induce forces on the wound through capillary action. The capillary pressure can be further increased by coating the matrices with bioactive molecules that bind to specific cell receptors such as fibronectin, Integrins, laminin and fibrin. This will allow a sponge to be produce that will apply micromechanical forces to the cells at the wound surface without the use of a vacuum. Control of the surface energy can be obtained by the density of the bioactive molecules placed on the surface of the matrix and on the porosity characteristics of the matrix.

Biomaterials will be critical to the function of these devices, as they must be non-toxic, non-immunogenic, and non-inflammatory while maintaining their structural characteristics. Several permanent biomaterials including polypropylene, polyethylene, Nylon, stainless steel, titanium, carbon, and silicone may be useful. In addition, biodegradable materials that interact with the wound in a predictable fashion may also be practicable; these include collagen, glycosaminoglycan, polylactic and polygalactic acid polymers, polydioxanone polyglyconate, and polyglecaprone. One important property of biomaterials is their pore structure; pores greater than 10 µm allow for vascular in-growth. For degradable polymers, the rate of degradation can be quantified based on tissue type and wound location. Changing the cross-link density, copolymerization, orientation and the degree of crystalinity of the polymer can control this degradation.

The sheet material can be fabricated from, or coated with, one or a combination of polymers to deliver drug. Examples of biocompatible polymers include, but are not limited to, ethylene-vinyl acetate copolymer (EV Ac), Poly-L-Lactic Acid (PLLA), alginate-heparin-sepharose, polyacrylic acid hydrogels, polyurethane, and polyurethane-polythelene oxide copolymers. The polymer can be made of one or a combination of biodegradable materials, such as, but not limited to, PLLA, polyglycolic acid, polycaprolactone, polyorthoesters, or fibrin matrices, all of which can incorporate drug for controlled release. Cross-linked gels of natural biomolecules, such as collagen or fibrin, or composed of synthetic peptides, nucleic acids, or carbohydrates, also may be utilized for this application.

In one embodiment, a feedback control system employing biosensors may be utilized for optimizing the rate of wound healing. Depending on the particular wound type, optimal strains and rates of strains can be time-dependent, or even dependent on the state of healing. Therefore, to use the system described in this disclosure to deliver optimal MicMF, a suitable mechanism must be designed to obtain data on the degree or lack of healing occurring in the wound. As described above, "smart" self-adjusting polymers represents a method for adapting force generation automatically to the state of wound healing. In addition to such implicit feedback regulation, a model of the invention is the use of an explicit feedback system in which biological parameters are measured and used to control the force generation or drug delivery. Biological or physical markers of wound healing can be used to detect such changes. Examples of such markers include either changes that are directly responsible for wound healing such as cellular proliferation, rate of neovascularization, or changes that are correlated with wound healing. For instance, a wound may become drier as it heals, its color may change, the level of the wound may rise, the compliance of the wound may increase, or any of these and other events may occur in combination to give an indication of wound development process. Alternately a lack of any of these markers may signal that the device is producing either a too high or a too low an output. For instance, if stretch rate is used to obtain wound healing, a greater or less than optimal rate for the wound in question may not produce the desired results.

Figure 7:
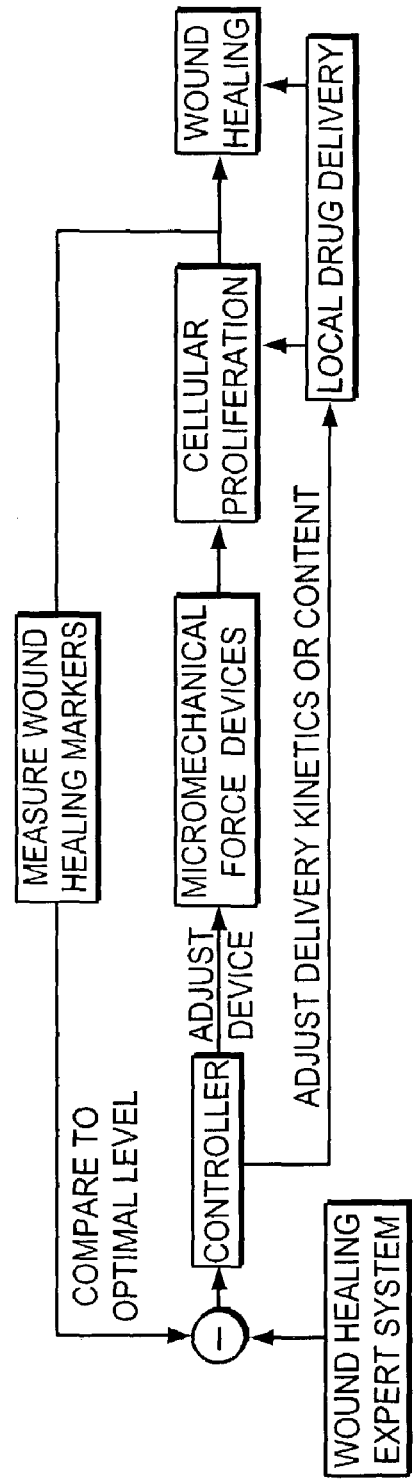
FIG. 7 is a block diagram indicating the sequence of a smart feedback control system according to an embodiment of the invention.
Figure 6A:
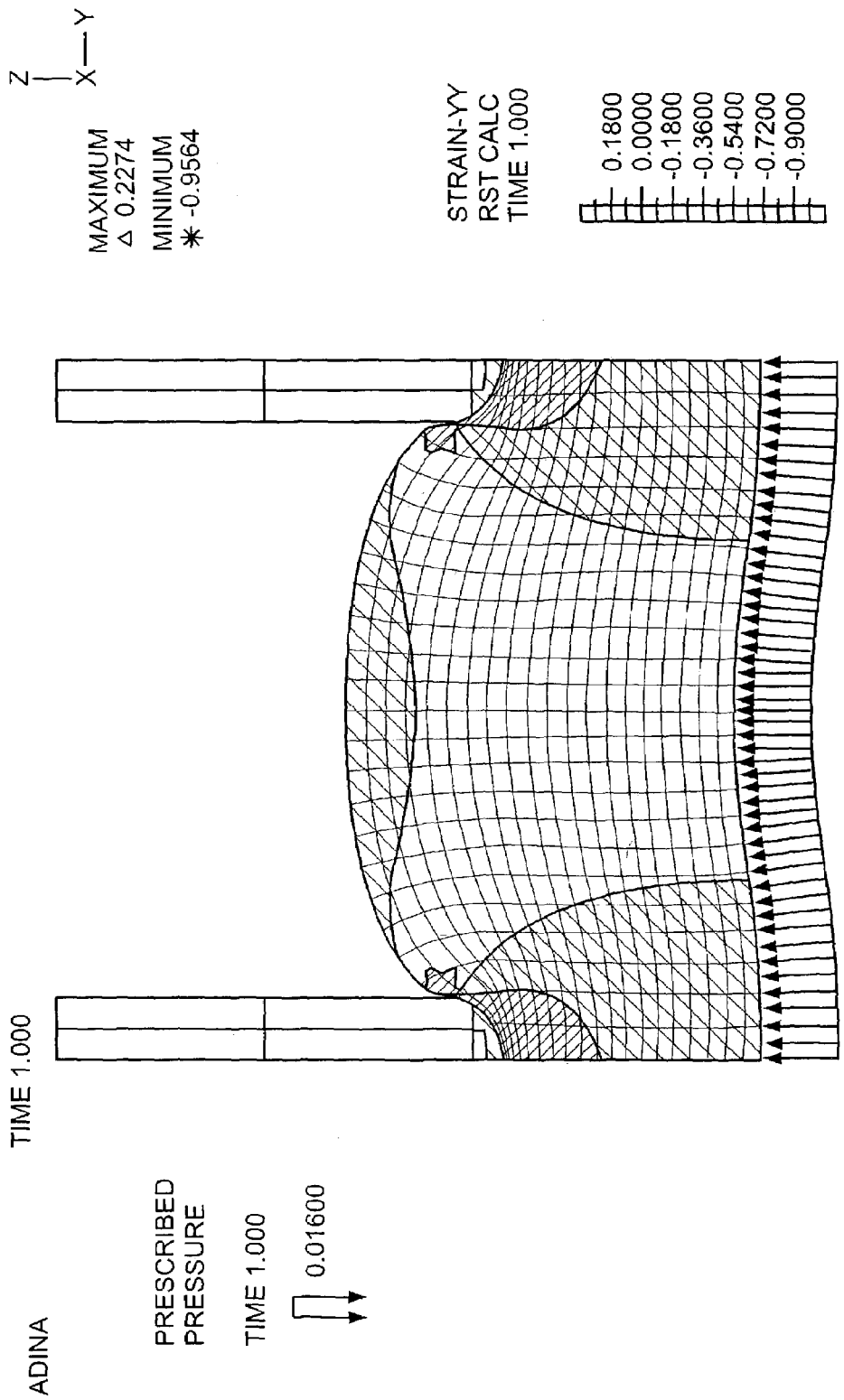
FIGS. 6A through 6D depict a finite element analysis of an embodiment of a porous sheet applied to a wound in which sub-atmospheric pressure has been applied.
Figure 6B:
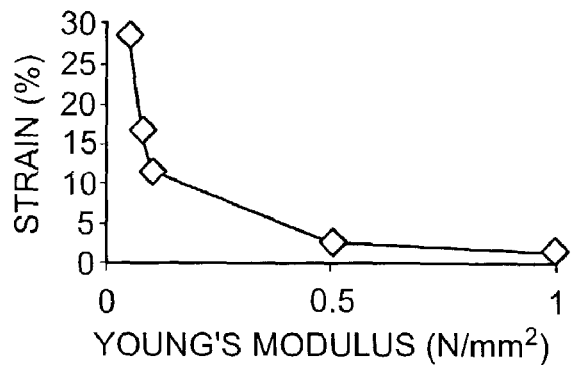
Figure 6C:
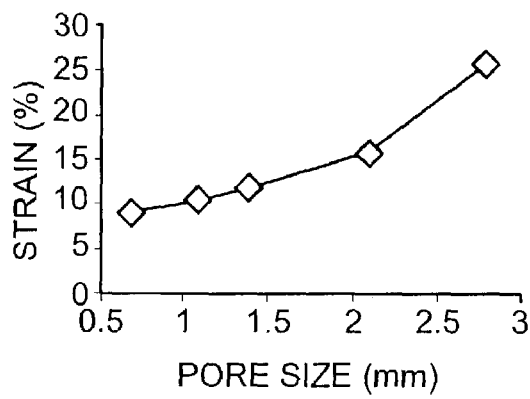
Figure 6D:
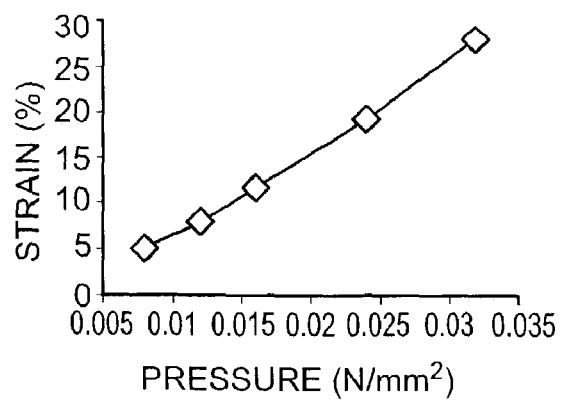

Sensor mechanisms that take advantage of the above markers might include a piezoelectric strain gauge mounted on the wound, a mechanical or optical device that measures the rising of the wound, an optical device that can detect color changes or hemoglobin levels (due to new vessel growth) in the wound, or other devices that can measure these changes. These sensors would input data into the expert control system that might output a change in the stretch rate, a change in the shear rate, a change in pressure, etc. These sensors can also direct a change in the level of drug delivery given to the wound. FIG. 7 presents a schema in which inputs to the sensor system are modified by the sensor based on the error it sees between the progress of wound healing and an optimal target parameter set.

Figure 10A:
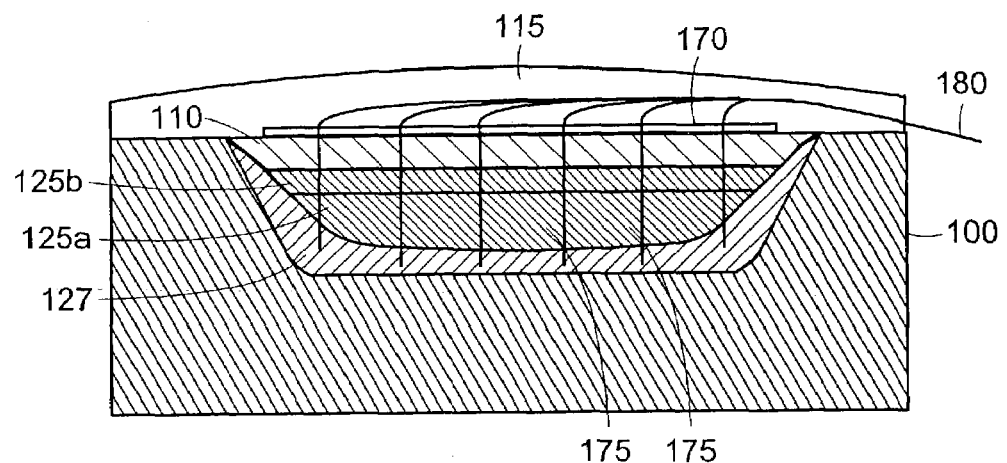
FIG. 10A is a schematic cross-section of a wound bed with an application of one embodiment of a therapeutic device according to the invention depicting a wound sensor array.
Figure 10B:
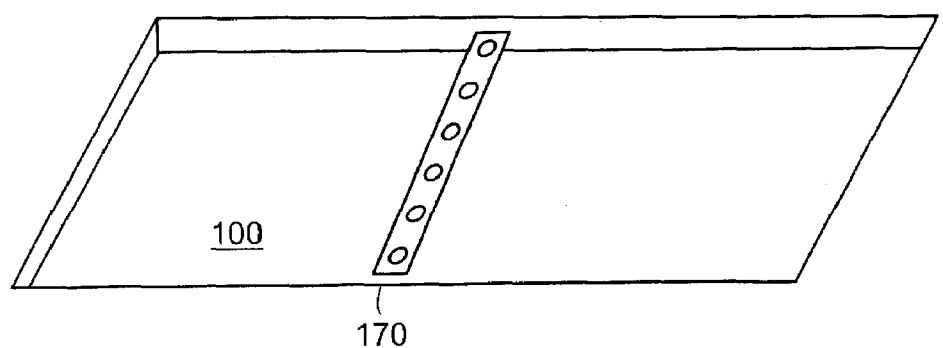
FIG. 10B is a schematic isometric diagram of a wound bed with an application of the device of FIG. 10A.
Figure 11A:
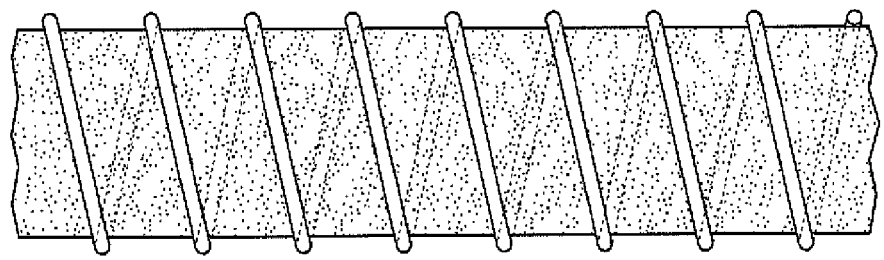
FIG. 11A is a schematic diagram of a compliant biodegradable tube with a stiff biodegradable wire coiled around the tube.
Figure 11B:
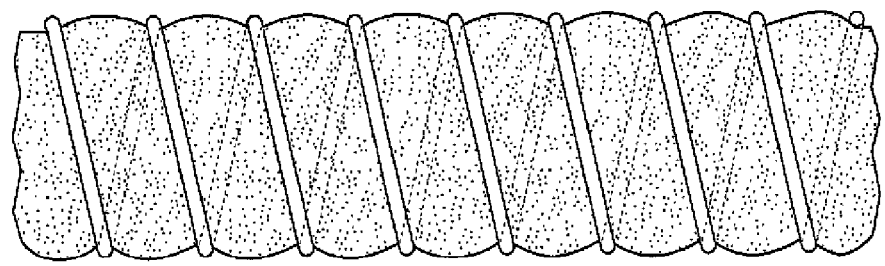
FIG. 11B is a schematic diagram of a compliant biodegradable tube with a stiff biodegradable wire coiled around the tube and wherein the tube is inflated such that the tube protrudes through the wire.
Figure 12A:
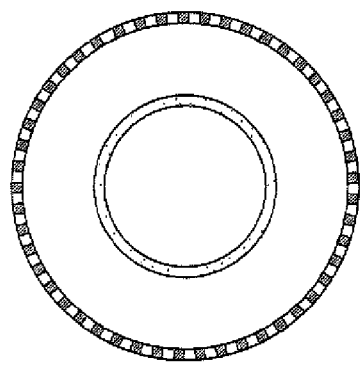
FIGS. 12A and 12B are cross-sectional views of the compliant biodegradable tube shown in FIGS. 11A and 11B, respectively.
Figure 12B:
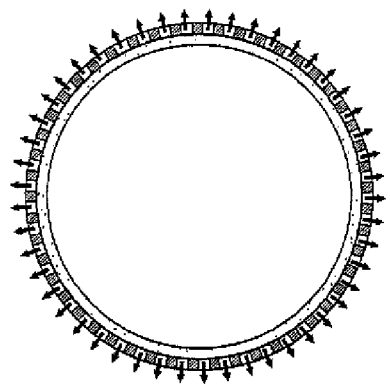

As shown in FIG. 10A, another embodiment of the invention may include a wound sensor array 170. The sensor array 170 is a multi-sensor designed to monitor the microenvironment of the wound bed 100. The parameters measured include wound temperature, pH, perfusion, pO2, pCO2, and glucose. The multisensor 170 can be placed through the biodegradable matrix 105 into the wound 100 itself to a depth of 1 to 3 mm. The sensor 170 array can be placed at any point in the wound 100 and multiple sensor probes 175 can be used to monitor the wound 100 at different points. As shown in FIG. 10B and in one embodiment, the sensor array 170 may comprise a linear arrangement. Alternatively, the size and configuration of the sensor array may adapted for a specific wound and tissue type. The disparate sensor probes 175 are entrained in the matrix 105 and fed through the occlusive dressing 115 to a sensor output 180. This sensor output 180 provides valuable information about the wound microenvironment that can lead to changes in managing the patient.

A finite element model can predict optimal pore design of non-degradable materials such as polyurethane. The wound can be modeled as an isotropic linearly elastic tissue in two dimensions with a fine mesh applied. Applying micromechanical forces to the wounds so that the surface is stretched by 5 to 20 percent will induce cellular division and application of cytokines. The finite element model allows calculation of optimal force application to a variety of biological tissues that can be characterized by their stiffness or Young's modulus of elasticity. Some tissues such as mucosa and fat are very pliable, others such as dermis and fascia stiffer, and tissues such as cartilage and bone quite stiff. The finite element model allows optimal design of pore structure and optimization of applied sub-atmospheric pressure based on the stiffness of the wound tissue. (see diagrams at the end of the provisional patent).

All biomaterial surfaces can be modified by ionic, covalent, hydrogen or mechanical bonds of surface active agents, or polymers. In addition bioactive agents including antibiotics, RGD peptides, collagen, anticoagulants, heparin, glycosaminoglycans, and electrically or magnetically charged particles can be added to the device surface.

Addition of cells to the micromechanical devices will allow for production of soluble growth factors as well as additional cells to the wound. A method to seed cells within a collagen-GAG matrix to cause a functional restoration of the epidermis in a full-thickness wound. Studies have shown that lethally irradiated neonatal fibroblasts seeded onto a Nylon-collagen matrix increase the healing of partial thickness burns. The cells can be genetically engineered to secrete essential growth factors such as bFGF, EGF or KGF.

Devices designed to apply MicMFs to the wound are ideally suited as drug delivery devices. Drugs useful in the treatment of wounds include antibiotics: silver, silver nitrate, mafenide acetate, povodine iodine, silver sulfadiazene, macrolides, penicillins, cephalosporins, aminoglycocides and quinolones. Other drugs of use in wound healing include soluble growth factors, angiogenic factors, vitamins, peptides and genetic material. Incorporation of these drugs into the polymer construct of the device can be designed for controlled release over time.

Some embodiments of the invention can be made to be entirely automated, self-contained, and portable. For example, the entire roller-system or oscillating flat plate or forced injection assemblies can be built, together with feedback and controller systems, into a closed battery-powered unit that the patient can wear on top of the wound, thus allowing ambulation. Translation velocities and oscillation frequencies can be pre-programmed, or continuously adapted according the built-in biological expert system in the feedback and controller system. Drug delivery can similarly be injected into the moving fluid at pre-programmed times and continuously monitored by the feedback and controller system.

The invention may be embodied in other specific forms without departing from the spirit or essential characteristics thereof. Therefore, it must be expressly understood that the foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A therapeutic device for promoting tissue growth, said device comprising:
    a variable composition matrix for application to the tissue, said matrix having a plurality of pores;
    a compliant biodegradable tube wherein said tube is coated with ECM proteins and configured for inflation; and
    a stiff biodegradable wire, wherein said wire is coiled around an external wall of said tube; such that said tube when inflated protrudes through the wire so as to exert micro-mechanical forces on the tissue.

2. The device according to claim 1, wherein said tube comprises a plurality of dialysis-membrane sized pores.

3. A method for promoting tissue growth, said method comprising the steps of
    a. providing a therapeutic device comprising a variable composition matrix for application to the tissue, said matrix having a plurality of pores; a compliant biodegradable tube wherein said tube is coated with ECM proteins and configured for inflation; and a stiff biodegradable wire, wherein said wire is coiled around an external wail of said tube; such that said tube when inflated protrudes through the wire so as to exert micro-mechanical forces on the tissue,
    b. applying said matrix adjacent to the tissue; and
    c. delivering micro-mechanical forces to the tissue through said variable composition matrix.

4. The method of claim 3, further comprising monitoring the microenvironment of a wound bed of a patient with a sensor wherein the sensor comprises a piezoelectric gauge.

5. The method of claim 3, wherein the sensor measures at least one of wound temperature, wound perfusion, wound pH, wound $pO_2$, wound $pCO_2$, and wound glucose.

* * * * *